(12) United States Patent
Lem

(10) Patent No.: US 8,466,196 B2
(45) Date of Patent: Jun. 18, 2013

(54) ACETALS AS PERFUMING INGREDIENTS

(75) Inventor: George Lem, Geneva (CH)

(73) Assignee: Firmenich SA, Geneva (CH)

( * ) Notice: Subject to any disclaimer, the term of this patent is extended or adjusted under 35 U.S.C. 154(b) by 197 days.

(21) Appl. No.: 13/126,084

(22) PCT Filed: Nov. 12, 2009

(86) PCT No.: PCT/IB2009/055025
§ 371 (c)(1),
(2), (4) Date: Apr. 26, 2011

(87) PCT Pub. No.: WO2010/064158
PCT Pub. Date: Jun. 10, 2010

(65) Prior Publication Data
US 2011/0243868 A1    Oct. 6, 2011

(30) Foreign Application Priority Data

Dec. 1, 2008   (WO) .................. PCT/IB2008/055024

(51) Int. Cl.
*A61K 31/357* (2006.01)
*C07D 317/12* (2006.01)

(52) U.S. Cl.
USPC .......................................... 514/467; 549/430

(58) Field of Classification Search
USPC .......................................... 514/467; 549/430
See application file for complete search history.

(56) References Cited

FOREIGN PATENT DOCUMENTS

| GB | 819771 A | 9/1959 |
|---|---|---|
| GB | 1167776 A | 10/1969 |
| JP | 2003-137758 A | 5/2003 |

OTHER PUBLICATIONS

International Search Report and Written Opinion dated Mar. 9, 2010 for application No. PCT/IB2009/055025 filed Nov. 12, 2009.
S. Arctander, Perfume and Flavor Chemicals, 1969, Montclair, New Jersey, Nos. 651, 652, 656 and 1956.
Kawasaki, "Odor masking compositions containing fragrant substances for hair cosmetics," XP002568295, Database Caplus [Online], Chemical Abstracts Service, Database Accession No. 2003:371661, abstract—& JP 2003-137758 (May 14, 2003).

*Primary Examiner* — Taofiq A Solola
(74) *Attorney, Agent, or Firm* — Winston & Strawn LLP

(57) ABSTRACT

The present invention relates to the field of perfumery. More particularly, it concerns some acetal derivatives of 3-methyl citral of formula (I) wherein the dotted lines indicate the presence of a single or double bond; $R^1$ represents a hydrogen atom or a methyl or ethyl group, $R^2$ represents a hydrogen atom or methyl group; and each $R^3$, taken alone, simultaneously or independently, represents a $C_{1-3}$ alkyl or alkenyl group; or said $R^3$ groups, taken together, represent a $C_{2-6}$ hydrocarbon group optionally comprising an oxygen atom. The present invention concerns the use of said compounds in the perfumery industry as well as the compositions or articles containing said compounds.

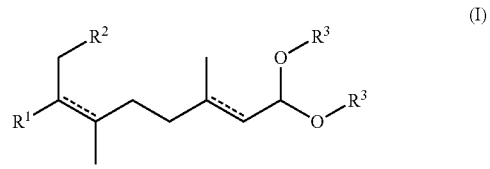

(I)

8 Claims, No Drawings

ACETALS AS PERFUMING INGREDIENTS

This application is a 371 filing of International Patent Application PCT/IB2009/055025 filed Nov. 12, 2009.

TECHNICAL FIELD

The present invention relates to the field of perfumery. More particularly, it concerns some acetal derivatives of 3-methyl citral. The present invention concerns the use of said compounds in the perfumery industry as well as the compositions or articles containing said compounds.

PRIOR ART

To the best of our knowledge, the compounds of formula (I), described herein below, are all new compounds.

The compounds with the closest chemical structure and being described as having valuable organolepic properties are some acetals of citral reported in the book by S. Arctander (Perfume and Flavor Chemicals, 1969, Montclair, N.J., USA), and specifically the diethyl (No 651), dimethyl (No 652) and the propyleneglycol (No 656) acetals. However these prior art compounds are reported as having always a citrus-lemon note type, in other words a quite different note from the present invention compounds. Nothing in the prior art suggests that the invention's compounds could have their specific odor (as reported further below) or even an odor at all.

DESCRIPTION OF THE INVENTION

We have now surprisingly discovered that a compound of formula

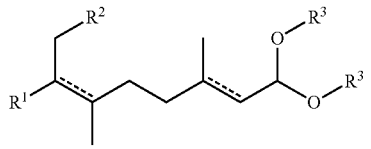

(I)

wherein the dotted lines indicate the presence of a single or double bond;
R$^1$ represents a hydrogen atom or a methyl or ethyl group, R$^2$ represents a hydrogen atom or methyl group; and
each R$^3$, taken alone, simultaneously or independently, represents a C$_{1-3}$ alkyl or alkenyl group; or said R$^3$ groups, taken together, represent a C$_{2-6}$ hydrocarbon group optionally comprising an oxygen atom;
can be used as perfuming ingredient, for instance to impart odor notes of the green type.

According to a particular embodiment of the invention, said compound (I) is a compound wherein the dotted lines indicate the presence of a single or double bond;
R$^1$ represents a methyl group and R$^2$ represents a hydrogen atom, or R$^2$ represents a methyl group and R$^1$ represents a hydrogen atom; and
each R$^3$, taken alone, simultaneously or independently, represents a C$_{1-3}$ alkyl group;
or said R$^3$ groups, taken together, represent a C$_{2-6}$ hydrocarbon group.

According to a particular embodiment of the invention, said compound (I) is a compound of formula

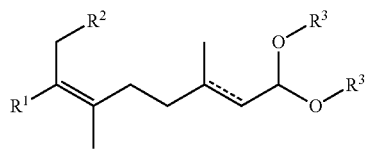

(II)

wherein the dotted line indicates the presence of a single or double bond;
R$^1$ represents a methyl group and R$^2$ represents a hydrogen atom, or R$^2$ represents a methyl group and R$^1$ represents a hydrogen atom; and
each R$^3$, taken alone, simultaneously or independently, represents a C$_{1-3}$ alkyl group, e.g. a linear one; or said R$^3$ groups, taken together, represent a C$_{2-5}$ hydrocarbon group.

According to a particular embodiment of the invention, said compound (II) is a compound wherein the dotted line indicates the presence of a double bond;
R$^1$ represents a methyl group and R$^2$ represents a hydrogen atom; and
the R$^3$ groups, taken together, represent a C$_{2-4}$ hydrocarbon group, such as CH$_2$CH$_2$, CH$_2$CH$_2$CH$_2$, CHMeCH$_2$, CHMeCHMe, CH$_2$CHMeCH$_2$ or CH$_2$CMe$_2$CH$_2$.

It is understood that the compounds of formula (I) can be in the form of any one of its E or Z isomers or stereoisomers as well as a mixture thereof.

For the sake of clarity, by the expression "the dotted lines indicate the presence of a single or double bond", or the similar, it is meant the normal meaning understood by a person skilled in the art, i.e. that the whole bonding (solid and dotted line) between the carbon atoms connected by said dotted line can be a carbon-carbon single or a double bond.

The invention's compounds are new compounds and therefore are another object on the invention.

As typical examples of the invention's compounds, one may cite 2-[(1Z)-2,5,6-trimethyl-1,5-heptadienyl]-1,3-dioxolane. Said compound possesses a green, herbal odor, evoking the Clary Sage with, a nice velvety side and violet leaf undertone. This compound is totally lacking lemon-citrus notes.

The odor of the invention's compounds lacks, or does not possess significant, citrus-lemon notes, which are characteristic of the prior art compounds and in particular of the above-mentioned citral acetals. Said differences lend the invention's compounds and the prior art compounds to be each suitable for different uses, i.e. to impart different organoleptic impressions.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)", it has to be understood here also the use of any composition containing compound (I) and which can be advantageously employed in perfumery industry as active ingredients.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids : Stabilisatoren, Dickungs- and Gehermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion ; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and ii) a consumer product base;

is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric softeners, fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 15% by weight, or even more, of the compounds of the invention based on the weight of the composition into which they are incorporated. Concentrations lower than these, such as in the order of 0.001% to 5% by weight, can be used when these compounds are incorporated into perfumed articles, percentage being relative to the weight of the article.

The invention's compounds can be prepared from the known compound Methyl Citral (Arctander No 1956) by reacting said starting material with a suitable alcohol or diol. A typical example is provided in the Examples herein below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

2-(Z-2,5,6-Trimethyl-hepta-1,5-dienyl)-[1,3]dioxolane

A 3 liter 3-neck flask equipped with a thermometer, magnetic stir bar and Dean-Stark trap is charged with 675 g of E- and Z-Methyl-citral (4.07 mol), 1210 g of ethylene glycol (19.5 mol), 23.3 g of $MgCl_2$ (0.24 mol) and 844 g of toluene. The entire mixture is refluxed for 27 hours during which time water and some ethylene glycol are azeotropically removed from the reaction until 92% of the starting material is consumed. After cooling the reaction mixture to room temperature, the lower phase containing unreacted ethylene glycol is discarded and the upper toluene phase is washed with saturated $NaHCO_3$ then water. After removal of toluene at reduced pressure, the crude concentrate is flash distilled under vacuum to give 789 g of 95% pure E- and Z-Methyl-citralacetal (E/Z=57/43). The latter is then carefully fractionated by distillation to give a total of 678 g of distillate of which 133 g is pure Z-Methyl-citralacetal and 222 g is pure E-Methyl-citralacetal.

$^{13}C$-NMR: 18.48, 20.07, 20.56, 23.72, 31.28, 33.73, 64.89, 100.155, 121.73, 124.71, 127.16, 145.27

$^1H$-NMR: 1.64 (s, 3H), 1.66 (b.s., 6H), 1.80 (d, J=1,3H), 2.15 (b.s., 4H), 3.86 (m, 2H), 4.00 (m, 2H), 5.24 (d.d., J=1, J=7, 1H), 5.47 (d, J=7, 1H).

Example 2

Preparation of a Perfuming Composition

A perfume, having an orange flower-green connotation, was prepared by admixing the following ingredients:

| Ingredient | Parts by weight |
|---|---|
| Terpenyl acetate | 1350 |
| 10%* Celery essential oil | 50 |
| 10%* Damascone Alpha | 370 |
| Habanolide ® [1] | 350 |
| Hedione ® [2] | 300 |
| Hivernal ® [3] | 100 |
| Iso E Super ® [4] | 250 |
| Lilial ® [5] | 2000 |
| 10%* Neobutenone ® [6] | 30 |
| Neroli oil | 1500 |
| Phenethylol | 250 |
| Amyl salicylate | 400 |
| Sclareolate ® [7] | 1250 |
| Yara Yara | 300 |
| 2,4-Dimethyl-3-cyclohexene-l-carbaldehyde | 500 |
| | 9000 |

* in dipropyleneglycol
[1] pentadecenolide; origin: Firmenich SA, Switzerland
[2] methyl dihydrojasmonate; origin: Firmenich SA, Switzerland
[3] 3-(3,3/1,1-dimethyl-5-indanyl)propanal; origin: Firmenich SA, Switzerland
[4] 1-(octahydro-2,3,8,8-tetramethyl-2-naphtalenyl)-1-ethanone; origin: International Flavors & Fragrances, USA
[5] 3-(4-tert-butylphenyl)-2-methylpropanal; origin: Givaudan SA, Switzerland
[6] 1-(5,5-dimethyl-1-cyclohexen-1-yl)-4-penten-1-one; origin: Firmenich SA, Switzerland
[7] propyl (S)-2-(1,1-dimethylpropoxy)propanoate; origin: Firmenich SA, Switzerland The addition of 1000 parts by weight of 2-(Z-2,5,6-Trimethyl-hepta-1,5-dienyl)-[1,3]dioxolane to the above-described perfuming composition imparted herbaceous-sage note and reinforced the green note provided by 2,4-dimethyl-3-cyclohexene-1-carbaldehyde.

When instead of the invention's compound were added the same amounts of Citral diethyl acetal (Artcander 651), Citral dimethyl acetal (Artcander 652) or Citral propyleneglycol acetal (Artcander 656), then the perfume acquired a clear and dominant lemon peel connotation.

What is claimed is:
1. 2-[(1Z)-2,5,6-trimethyl-1,5-heptadienyl]-1,3-dioxolane.
2. A method to confer, enhance, improve or modify the odor properties of a perfuming composition or of a perfumed article, which method comprises adding to the composition or article an effective amount of 2-[(1Z)-2,5,6-trimethyl-1,5-heptadienyl]-1,3-dioxolane to provide a green, herbal odor, evoking Clary Sage with a velvety and violet leaf undertone while totally lacking lemon-citrus notes.
3. The method of claim 2, wherein the perfuming composition further comprises at least one ingredient selected from the group consisting of a perfumery carrier and a perfumery base; and optionally, at least one perfumery adjuvant.
4. The method of claim 2, wherein the perfumed article further comprises a consumer product base.
5. The method of claim 4, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.
6. A perfuming a composition comprising
 i) the compound according to claim 1 in an amount effective to provide a green, herbal odor, evoking Clary Sage with a velvety and violet leaf undertone while totally lacking lemon-citrus notes;
 ii) at least one ingredient selected from the group consisting of a perfumery carrier and a perfumery base; and
 iii) optionally at least one perfumery adjuvant.

7. A perfumed article comprising:
i) the compound according to claim 1 in an amount effective to provide a green, herbal odor, evoking Clary Sage with a velvety and violet leaf undertone while totally lacking lemon-citrus notes; and
ii) a consumer product base.

8. The perfumed article according to claim 5, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *